US008377692B2

(12) United States Patent  
Fulga et al.

(10) Patent No.: US 8,377,692 B2  
(45) Date of Patent: Feb. 19, 2013

(54) PROCESS FOR THE MANUFACTURING OF HUMAN MONONUCLEAR PHAGOCYTIC LEUKOCYTES

(75) Inventors: Valentin Fulga, Tel-Aviv (IL); Ronit Kleiner Bakimer, Tel-Aviv (IL); Issar Ash, Rehovot (IL); Michal Eisenbach-Schwartz, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 575 days.

(21) Appl. No.: 10/496,352

(22) PCT Filed: Nov. 21, 2002

(86) PCT No.: PCT/IL02/00930

§ 371 (c)(1),
(2), (4) Date: Feb. 8, 2005

(87) PCT Pub. No.: WO03/044037

PCT Pub. Date: May 20, 2003

(65) Prior Publication Data

US 2005/0129663 A1 Jun. 16, 2005

Related U.S. Application Data

(60) Provisional application No. 60/331,780, filed on Nov. 21, 2001.

(51) Int. Cl.  
*C12N 5/00* (2006.01)
(52) U.S. Cl. ........ 435/377; 435/325; 435/375; 424/93.7
(58) Field of Classification Search .................. None  
See application file for complete search history.

(56) References Cited

U.S. PATENT DOCUMENTS

| | | | |
|---|---|---|---|
| 4,086,057 A | | 4/1978 | Everett |
| 5,292,655 A | * | 3/1994 | Wille, Jr. ................... 435/384 |
| 5,800,812 A | | 9/1998 | Eisenbach-Schwartz et al. |
| 6,043,089 A | | 3/2000 | Sugiyama et al. |
| 6,060,515 A | * | 5/2000 | Elias et al. ................... 514/560 |
| 6,117,424 A | | 9/2000 | Eisenbach-Schwartz et al. |
| 6,251,943 B1 | * | 6/2001 | Barrett et al. ................. 514/564 |
| 6,267,955 B1 | | 7/2001 | Eisenbach-Schwartz et al. |
| 2002/0072806 A1 | * | 6/2002 | Buskirk et al. .............. 623/23.51 |
| 2003/0109583 A1 | * | 6/2003 | Raju et al. ..................... 514/563 |

FOREIGN PATENT DOCUMENTS

| | | |
|---|---|---|
| WO | 98/41220 A1 | 9/1998 |
| WO | 99/50391 A1 | 7/1999 |

OTHER PUBLICATIONS

Definition of "sterile" from Merriam-Webster online medical dictionary hosted by the National Library of Medicine. Accessed online at <http://www.nlm.nih.gov/medlineplus/mplusdictionary.html>. 1 page, Accessed 2009.*

Fuhlbrigge RC et al. 1987. Regulation of interleukin 1 gene expression by adherence and lipopolysaccharide. J Immunol 138: 3799-3802.*

Cohn ZA et al. 1965. The differentiation of mononuclear phagocytes. J Exp Med 121: 153-170.*

C. Sepulveda-Merriil et al, "Antigen-presenting capacity in normal human dermis is mainly subserved by CD1a + Cells", British Journal of Dermatology, 1994, vol. 131, pp. 15-22.

O. Lazarov-Spiegler et al, "Restricted Inflammatory Reaction in the CNS: a Key Impediment to Axonal Regeneration?", Molecular Medicine Today, Aug. 1998, pp. 337-342.

O. Rapalino et al, "Implantation of Stimulated Homologous Macrophages Results in Partial Recovery of Paraplegic Rats", Nature Medicine, Jul. 1998, vol. 4, pp. 814-821.

Mical Schwartz, "Macrophages and Microglia in Central Nervous System Injury: Are They Helpful or Harmful?", Journal of Cerebral Blood Flow & Metabolism, 2003, vol. 23, pp. 385-394.

Roitt et al. "Illustrated Immunology", Nankodo Co., Ltd., Japan, pp. 35-38 (1990).

Dougherty et al., "Brain Derived Neurotrophic Factor in Astrocytes, Oligodendrocytes, and Microglia/Macrophages after Spinal Cord Injury" Neurobiology of Disease, 7: 574-585 (2000).

Prewitt et al., "Activated Macrophage/Microglial Cells Can Promote the Regeneration of Sensory Axons into the injured Spinal Cord" Experimental Neurology 148: 433-443 (1997).

Ishikawa., "Function and Structure of Skin" Medicine vol. 37(4): 508-511 (2000).

Jones et al., "Prevalence of Important Pathogens and Antimicrobial Activity of Parenteral Drugs at Numerous Medical Centers in the United States I. Study on the Threat of Emerging Resistences: Real or Perceived?" Diagn. Microbiol. lnfec. Dis. 10: 203-215 (1994).

Rediske et al., "Pulsed Ultrasound Enhances the Killing of *Escherichia coli* Biofilms by Aminoglycoside Antibiotics in Vivo" Antimicro Agents Chemother 44(3): 771-772 (2000).

Comfort et al., "The prevention of contamination of teeth stored for transplantation" Oral surg 49(3): 200-203 (1980).

Rediske et al., "Ultrasonic Enhancement of Antibiotic Action on *Escherichia coli* Biofilms: an In Vivo Model" Antimicro Agents Chemother 43(5): 1211-1214, 1999.

Ahmed et al., "Sterilization of Teeth for Homogenous Transplantation" British J Oral Surg 14: 143-149 (1976).

Roitt et al. "Immunology", Gower Medical Publishing Ltd., London, England. pp. 2.8-2.15. (1985).

(Continued)

*Primary Examiner* — Lora E Barnhart Driscoll

(74) *Attorney, Agent, or Firm* — Browdy and Neimark, PLLC

(57) ABSTRACT

A process for the manufacture of human mononuclear phagocytic leukocytes comprises incubating monocytes isolated from a blood sample of an individual and skin segments from the same individual, removing the dermis segments from the incubation mixture and sedimenting the obtained activated mononuclear phagocytic leukocytes by centrifugation, washing and resuspending the activated phagocytic leukocytes in the medium, and evaluating the culture for its suitability for human administration. Cellular therapy products are made from the obtained cultures and are useful for promoting axonal regeneration in the CNS, wound healing and treatment of myocardial infarction.

12 Claims, 1 Drawing Sheet

OTHER PUBLICATIONS

Colotta et al., "Expression of monocyte chemotactic cytokine by human mononuclear phagocytes". J. Immunol., 148(3) p. 760-765 (1992).

Neumeister et al., "Induction of cytokines and expression of surface receptors in Mono Mac 6 cells after infection with different *Legionella* species", APMIS 106: 319-333 (1998).

Roberts et al., "Effects of *Porphyromonas gingivalis* and *Escherichia coli* lipopolysaccharides on mononuclear phagocytes", Infect. Immunity 65(8): 3248-3254 (1997).

Salamon et al., "Accessory function of human mononuclear phagocytes for lymphocyte responses to the superantigen Staphylococcal Enterotoxin B", Cell. Immunol., 141:466-484 (1992).

Lopez et al., "The Regulation of Neurotrophic Factor Activities Following HIV-1 Infection and Immune Activation of Mononuclear Phagocytes" Poster presented at 9th Conference on Retroviruses and Opportunistic Infections (2002), Seattle, WA Feb. 24-28; available online at: http://www.retroconference.org/2002IPosters/13694.pdf.

Chen et al.;"Effect of Cordyceps Sinensis on the proliferation and differentiation of human leukemic U937 cells" Life Sciences 60(25):2349-59 (1997).

Nakada et al. "[English Translation of title: ]45. Control of Surgery Equipment by an ultra-sound wave cleaning machine during surgery" Ikigaku, vol. 70, No. 10, p. 531-532 (2000). (Japanese).

Kobayashi et al. "BDNF and NT-4/5 prevent atrophy of rat rubrospinal neurons after cervical axotomy, stimulate GAP-43 and Talpha1-tubulin mRNA expression, and promote axonal regeneration" The Journal of Neuroscience 17 (24):9583-95 (1997).

Menei et al. "Schwann cells genetically modified to secrete human BDNF promote enhanced axonal regrowth across transected adult rat spinal cord" European Journal of Neuroscience 10(2):607-21 (1998).

Ye et al. "Treatment of the chronically injured spinal cord with neurotrophic factors can promote axonal regeneration from supraspinal neurons" Experimental Neurology 143(1):70-81 (1997).

English Translation of Official Action for Japanese Patent Appln. No. 2010-018379, mailed Sep. 3, 2010.

* cited by examiner

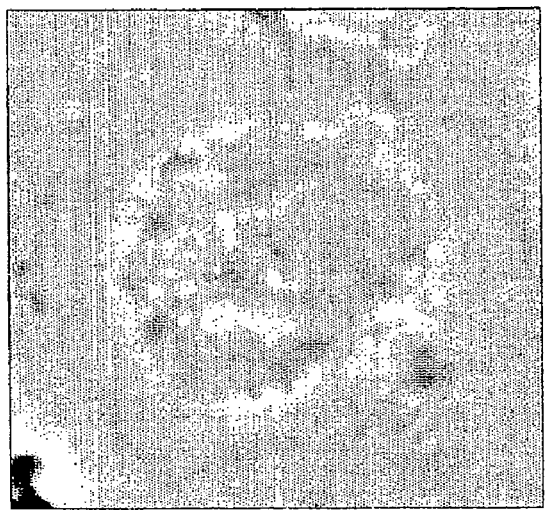 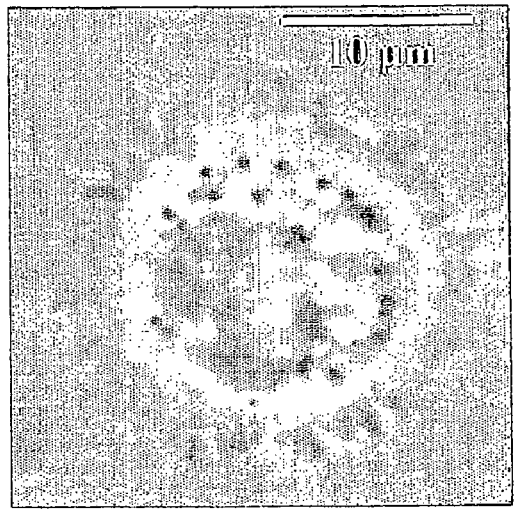
1A                    1B

PROCESS FOR THE MANUFACTURING OF HUMAN MONONUCLEAR PHAGOCYTIC LEUKOCYTES

FIELD AND BACKGROUND OF THE INVENTION

The present invention relates to a process for the manufacture of human mononuclear phagocytic leukocytes, to a culture of the cells obtained thereby and to the uses thereof.

Healing of injured tissue is a complex natural process based on the synchronized interaction between many molecular and physiological factors. An effective inflammatory response is one of the principal elements inducing regeneration and repair of damaged tissue. This is one of the earliest and most crucial reactions of tissues with regenerative capacity. The macrophages, which are recruited and further activated in situ, are key agents in the initiating stages of an effective inflammatory reaction. The inflammatory reaction is an integral part of wound healing in all the tissues in the body.

Following axonal injury, neurons of the mammalian peripheral nervous system (PNS) have a greater capacity than the central nervous system (CNS) for axonal regeneration and macrophages were shown to play a key role in PNS axonal regeneration (Schwartz et al., 1989, FASEB J., 3:2371-2378).

The mammalian CNS shows a poor capacity for axonal regeneration following axonal injury. The difference between axonal regeneration in the CNS and PNS seems to be due mainly to the cellular environment of the neurons than to the neurons themselves. Following neuronal injury, the Schwann cells that surround PNS neurons are modulated so as to become permissive or supportive for axonal regeneration, while the astrocytes, oligodendrocytes and microglia that surround CNS neurons do not show such modulation and remain unsupportive or inhibitory for axonal regeneration.

Differences in the post-injury inflammatory response are correlated with this lack of modulation. In particular, the accumulation of mononuclear phagocytes in response to CNS injury is delayed and limited in comparison with the response to injury in the PNS.

In the CNS, the inflammatory reaction is decreased, at least partly, due to the relative ineffectiveness of resident tissue macrophages (microglia). This deficit is further enhanced by the inability of blood-borne monocytes to enter the CNS and to act as they normally do in any other injured tissue in need of wound healing.

In U.S. Pat. Nos. 5,800,812, 6,117,424 and 6,267,955, all assigned to the same applicant of the present application, each and all of these patents being herein incorporated by reference as if fully disclosed herein, methods and compositions have been disclosed for the use of allogeneic mononuclear phagocytes to promote axonal regeneration in the CNS of a mammal. These patents describe methods for the isolation and culture of monocytes isolated from peripheral blood from adult Sprague-Dawley rats, and for the stimulation of the isolated monocytes by coincubation with syngeneic rat sciatic or optic nerve segments or by culture with medium conditioned by syngeneic rat sciatic nerve or optic nerve. The stimulated monocytes were then assayed for phagocytic activity and/or nitric oxide production and administered to rats that have been subjected to optic nerve transection at or near the site of injury.

SUMMARY OF THE INVENTION

It is an object of the present invention to provide a process for the manufacture of human mononuclear phagocytic leukocytes.

It is another object of the present invention to provide a process for the manufacture of such human mononuclear phagocytic leukocytes which express wound-healing phenotypes.

It is a further object of the present invention to provide a process for the manufacture of such human mononuclear phagocytic leukocytes which express wound-healing phenotype and are suitable for promoting axonal regeneration, for example in cases of spinal cord injury.

It is still another object of the present invention to provide a process for the manufacture of such human mononuclear phagocytic leukocytes which express wound-healing phenotypes and are suitable for healing of skin wounds, particularly chronic skin ulcers.

It is yet another object of the present invention to provide a process for the manufacture of such human mononuclear phagocytic leukocytes which express wound-healing phenotypes and are suitable for reducing the volume of necrotic tissue, for example in cases of myocardial infarction.

It is still a further object of the present invention to provide methods for the characterization of such human mononuclear phagocytic leukocytes produced by the process of the invention, which express wound-healing phenotypes.

These and other objects of the invention are provided by a process in which monocytes are isolated from the blood of an individual, suspended in a medium suitable for the culture of monocytes, and incubated either with tissue-engineered skin or with skin tissue removed from the same individual, preferably dermis, followed by removal of the skin fragments, washing of the macrophages and resuspension of the obtained activated mononuclear phagocytic leukocytes in the same suitable medium used before.

In a preferred embodiment of the invention, the human mononuclear phagocytic leukocytes are autologous, namely they are prepared from peripheral blood monocytes of an individual and are activated with skin tissue of the same individual to whom they will be administered The invention further provides cellular therapy preparations for promotion of axonal regeneration in the CNS, particularly after CNS injury, for wound healing and for reduction of necrotic tissue in myocardial infarction.

BRIEF DESCRIPTION OF THE FIGURE

FIGS. 1A-1B are photographs of a non-granulated monocyte (before incubation) and of a granulated mononuclear phagocytic leukocyte (after incubation), respectively.

DETAILED DESCRIPTION OF THE INVENTION

Phagocytes are defined as cells capable of ingesting particulate matters such as microorganisms and other particulate antigens that are opsonized, and include cells such as macrophages and monocytes.

Monocytes are mononuclear phagocytic leukocytes. Formed from hematopoietic cells in the bone marrow from promonocytes, monocytes enter the blood, circulate for up to 72 hours and subsequently enter tissues such as the lung, liver, and diseased tissues such as malignant tumors and atherosclerotic plaques, where they become macrophages. Differentiation of monocytes into macrophages involves a number of changes: change in morphology, increase in size, increase in phagocytic activity, expression of cellular markers, higher levels of lytic enzymes and secretion of a variety of soluble factors.

Macrophages are dispersed throughout the body. Some take up residence in particular tissues becoming fixed macrophages, whereas others remain motile and are called free macrophages.

Although normally in a resting state, macrophages are activated by a variety of stimuli in the course of an immune response. Phagocytosis of particulate antigens serves as an initial activating stimulus. However, macrophage activity can be further enhanced by cytokines secreted by activated T helper ($T_H$) cells, such as interferon-gamma, by mediators of the inflammatory response, and by bacterial cell-wall products.

Monocytes are among the first cells taking part in the inflammatory process. They have numerous tasks and the degree of their activation probably enables them to perform their duties. The process of monocytes' activation is not an all-or-non phenomena, but a gradual, stimulus-specific response.

The numerous functions of the monocytes/macrophages are directly related to the degree of their activation and include immune, secretory, phagocytic and other functions. It is conventional to define three different groups of macrophages, characterized according to the extent of their activation:

(i) wound healing macrophages, that function primarily as first sentries in the inflammatory reaction;

(ii) antimicrobial and cytotoxic macrophages, that function primarily in the body defense mechanisms against pathogenic organisms and malignant cells; and (iii) antigen-presenting macrophages, that assist cells involved in any inflammatory reaction, particularly TH cells, in their function.

As used herein in the application, the terms "mononuclear phagocytic leukocytes", "mononuclear leukocytes", "mononuclear phagocytes" and "macrophages" are used interchangeably to designate the cells manufactured by the process of the invention.

In one embodiment, the present invention provides a process for the manufacture of human mononuclear phagocytic leukocytes, comprising:

(i) isolating monocytes from a blood sample of an individual and suspending the monocytes in a suitable medium (herein "the medium");

(ii) processing skin segments from the same individual, removing the epidermis, sonicating the dermis segments in the medium in the presence of antibiotics, soaking the sonicated dermis segments in the fresh medium in the presence of antibiotics, and rinsing with the fresh medium in the absence of antibiotics;

(iii) coincubating the monocytes of step (i) with rinsed dermis segments of step (ii);

(iv) removing the dermis segments from the incubation mixture and sedimenting the obtained activated mononuclear phagocytic leukocytes by centrifugation;

(v) washing and resuspending the activated mononuclear phagocytic leukocytes in the medium; and (vi) evaluating the culture for its suitability for human administration.

In step (i), the human monocytes may be isolated from a blood sample by any conventional method. In one embodiment, the method for isolation of monocytes comprises the following steps:

(a) dilution of blood;

(b) separation of the mononuclear cell fraction by layering the diluted blood of step (a) onto Ficoll followed by centrifugation;

(c) washing the cells separated in step (b) and submitting them to a further separation by density gradient centrifugation on Percoll; and (d) washing the separated monocyte-enriched fraction from step (c) and suspending the cells in a suitable medium.

The dilution of whole blood in step (a) and washing of cells in steps (c) and (d) above may be carried out with phosphate-buffered saline (PBS), and the monocyte-enriched fraction in step (d) above may be suspended in a suitable medium.

As used herein, the term "suitable medium" means a medium suitable for culture of monocytes such as, but not limited to, Iscove's Modified Dulbecco's Medium (IMDM) and RPMI 1640. Both the processing of the monocytes and of the skin segments are carried in this same suitable medium.

In step (ii) of the process for manufacture of the human mononuclear phagocytic leukocytes, the processing of the human skin segments may be carried out by freezing skin fragments from the same individual, thawing and soaking the skin fragments with a washing solution consisting of the suitable medium, e.g. IMDM or RPMI 1640, and antibiotics, and then cutting into segments before removal of the epidermis, thus obtaining dermis segments of about 0.1 to 5 $cm^2$ (area of the upper surface of the skin segments), preferably about 0.5 to 2.0 $cm^2$, or even less. The dermis segments are then put in a sterile plastic container in which they are immersed in the same suitable medium containing antibiotics such as, but not limited to, ofloxocin, vancomycin and gentamicin, the container is introduced in an ultrasonic bath containing deionized water and sonicated. The sonicated dermis segments are then soaked in fresh suitable medium containing the same antibiotics and rinsed with fresh medium in the absence of said antibiotics. The dermis segments may be sonicated, for example, in an ultrasonic bath at the frequency of 35-40 kHz.

In the incubation step (iii), the dermis segments, after sonication, are soaked in fresh suitable medium containing antibiotics and rinsed with the same medium free of antibiotics, and are then incubated with the monocytes at about 36-38° C. in an atmosphere of 5% $CO_2$ for up to 38 hours. The dermis segments are then removed from the incubation mixture, the activated cells are recovered by centrifugation, washed and resuspended in the fresh suitable medium, preferably IMDM.

In one preferred embodiment of the invention, both the blood sample for the isolation of the monocytes and the skin tissue for activation of the monocytes are autologous, namely they are obtained from the patient to whom the activated mononuclear phagocytic leukocytes will be administered. However, also the use of allogeneic monocytes and skin tissue is envisaged by the present invention but, preferably, they should be from the same individual.

In another embodiment of the invention, the skin tissue in step (ii) can be replaced by a tissue-engineered skin. Any available tissue-engineered skin or tissue-engineered skin equivalent such as artificial skin, either those containing living cells or those not containing living cells, can be used according to the invention. In case the tissue-engineered skin has no living cells, the steps of treatment with antibiotics are not performed.

In step (vi), in order to characterize the cells suitable for human administration, some or all of the following tests are performed on a sample of the batch of the obtained activated mononuclear phagocytic leukocytes:

(a) Sterility—The cells should be free of contamination by bacteria, yeast and fungi. For the sterility test, the cells are filtered and tested to detect bacterial and fungal contamination in accordance with 21 CFR section 610.12;

(b) Cell viability—Culture viability is preferably tested using the well-known Trypan Blue staining exclusion method;

(c) Bacterial endotoxin test—The culture of cells is quantitatively tested for gram-negative bacterial endotoxin using the *Limulus Amebocyte* Lisate (LAL) test according to current USP;

(d) Gram staining—The presence or absence of bacteria is tested by the Gram stain technique;

(e) Morphometric analysis/cytoplasmic granules count by phase microscopy and comparison with the monocytes before incubation with the dermis segments—The morphometric analysis of the cells and count of the cytoplasmic granules under the phase microscope is a very important test for the activated macrophages;

(f) Assay of purity of the cell population by flow cytometry using monoclonal antibodies that detect the monocyte CD14 cell membrane marker;

(g) Interleukin-1β (IL-1β) assay, secreted in high levels by activated macrophages;

(h) Assay of mannose receptor expression of the cells after incubation by flow cytometry using monoclonal antibodies against the mannose receptor, that is expressed in higher levels by activated macrophages, and its comparison with the cells before incubation;

(i) Assay of ICAM-1 expression on the cell membrane by flow cytometry using monoclonal antibodies against the CD54 antibodies marker (ICAM-1), that is expressed in higher levels on the cell membrane after activation;

(j) Assay of brain-derived neurotrophic factor (BDNF) secretion by the activated macrophages; and (k) Assay of IL-6 secretion by the activated macrophages.

If the results are satisfactory, the whole batch of cells can then be used for cellular therapy of the individual.

While performing step (ii) of the process of the present invention, it was found that sonication of the skin tissue in the conditions described above also lead to decontamination of the skin tissue. Thus, in another aspect, the present invention provides a method for decontamination of skin tissue, preferably human skin tissue, more preferably human dermis segments, which comprises sonicating skin tissue in a suitable medium in the presence of antibiotics.

According to this method, human skin segments may be processed, followed by removing the epidermis, sonicating the dermis segments in a suitable medium (herein "the medium") in the presence of antibiotics, soaking the sonicated dermis segments in the fresh medium in the presence of antibiotics, and rinsing with the fresh medium in the absence of antibiotics. The processing of the human skin segments may be carried out by freezing skin fragments, thawing and soaking the skin fragments with a washing solution consisting of the suitable medium, preferably IMDM, and antibiotics, and then cutting into segments before removal of the epidermis, thus obtaining dermis segments of about 0.1 to 5 cm$^2$, preferably 0.5 to 2.0 cm$^2$, or less. For sonication, the dermis segments may be put in a sterile plastic container in which they are immersed in the suitable medium, preferably IMDM, containing antibiotics such as, but not limited to, ofloxocin, vancomycin and gentamicin, the container is introduced in an ultrasonic bath containing de-ionized water and sonicated, the sonicated dermis segments are then soaked in fresh medium, preferably IMDM, containing the same antibiotics and rinsed with fresh medium in the absence of said antibiotics. For example, the dermis segments may be sonicated in an ultrasonic bath at the frequency of 35-40 kHz.

The human mononuclear phagocytic leukocytes obtained according to the process of the invention have been characterized and they represent a novel cell population and as such constitute another aspect of the present invention.

It was found, in accordance with the present invention, that the most important characteristic of the activated human mononuclear phagocytic leukocytes obtained by the process of the present invention is the number of cytoplasmic granules. Under the phase microscope, these granules appear as highly refractive spheres with a bluish hue that can be easily counted, as exemplified in FIG. 1B herein.

Thus, in another aspect, the present invention provides a culture of human mononuclear phagocytic leukocytes, at least 25% of the most granular cells showing at least 4 granules per cell under the phase microscope. In one embodiment, preferably, at least 40%, more preferably 60% or more, of the cells are CD14$^+$. In another embodiment, the level of IL-1β produced by the cells is at least 17 pg/10$^6$ CD14$^+$ cells.

In a further embodiment, the present invention provides a culture of activated human mononuclear phagocytic leukocytes of the invention exhibiting at least the characteristics a-g from the characteristics a-k below:

(a) sterility of 14 days;

(b) culture viability of at least 80% using the Trypan Blue staining exclusion method;

(c) product release specification of less than 200 Eu/ml in the bacterial endotoxin test;

(d) no evidence of bacteria on Gram-stain;

(e) by morphometric analysis, at least 25% of the most granular cells show at least 4 granules per cell;

(f) at least 40%, preferably 60% or more, of the cells are CD14 positive (CD14$^+$);

(g) the level of IL-1 β produced by the cells is at least 17 pg/10$^6$ CD 14$^+$ cells;

(h) the activated cells show a statistically significant increase in the mannose receptor expression in comparison to non-activated monocytes from which they originated;

(i) the cells express the ICAM-1 receptor with geometric mean fluorescence of about 200 or higher;

(j) the cells secrete BDNF at a level higher than 10 pg/10$^6$ CD14$^+$ cells; and (k) the secretion of IL-6 by the activated cells is about 4-15 fold in comparison to the IL-6 secretion by non-activated monocytes from which they originated.

In another aspect of the present invention, a cellular therapy product is manufactured which consists of human activated mononuclear phagocytic leukocytes that have been incubated with skin (or only dermis) segments for up to 5 days, preferably up to 38 hours, and more preferably up to 24 hours. In one preferred embodiment, the starting monocytes and the dermis are autologous and are collected from the patient to whom the final product will be administered.

In a preferred embodiment, the cell culture intended for use as final product consists of human activated mononuclear phagocytic leukocytes of which at least 40%, and generally more than 50%, are macrophages. Monocytes are isolated from the patient's peripheral blood and then incubated with autologous skin (dermis prepared from full-thickness skin tissue) that has been harvested from the injured patient. The final cellular therapy product comprises 1-10 million macrophages suspended in a pharmaceutically acceptable carrier such as phosphate-buffered saline (PBS) or, preferably, in a culture medium such as IMDM or any other suitable cell culture medium such as RPMI 1640, but other suitable pharmaceutically acceptable carriers will readily be apparent to those skilled in the art.

The activated human mononuclear phagocytic leukocytes of the present invention express wound-healing phenotypes and can be beneficial in the treatment, inter alia, of the following conditions in humans:

(i) For promoting axonal regrowth after injury or disease situated in any portion of the CNS that results in or is accompanied by axonal damage such as, but not limited to, injuries in the brain, spinal cord or optic nerve. These injuries include spinal cord injury, trauma including blunt trauma, penetrating trauma, brain coup or contrecoup, trauma sustained during a neurosurgical operation or other procedure, and stroke including hemorrhagic stroke or ischemic stroke.

(ii) Healing of chronic skin ulcers. Macrophages resident in wounded tissue are not adequately activated by the skin at the margins of the ulcer and lack the ability to activate inflammatory cells as compared to normal skin tissue. Application of the activated macrophages into the wound will improve the chances for healing.

(iii) Reduction of the volume of the necrotic tissue in cases of myocardial infarction. The activated macrophages of the invention expressing wound-healing phenotypes are expected to be beneficial in the reduction of the volume of necrotic tissue in cases of myocardial infarction. Prolonged cessation or significant decrease of blood flow to the myocardium leads to cardiac muscle cells' death. Myocardial death induces decrease of cardiac function. Since myocytes are incapable of regeneration, the dead cardiac tissue is replaced by scar tissue which is not functional. From the aspect of regeneration, there is a strong similarity between the lack of regeneration ability of myocytes and of central nervous system axons. As shown before for the axons in the CNS, for example in U.S. Pat. No. 6,117,424, it is envisioned that also for the cardiac myocytes the reason for the inability to regenerate is not intrinsic to the cells themselves, but to the delayed and ineffective inflammatory reaction that takes place at the infarct site at the suitable time after ischemia due to insufficient numbers of macrophages which act at a low pace. The administration of the activated macrophages of the invention in situ, relatively early in the process of the infarction, may minimize the volume of the necrosis and thus save the cardiac function.

The activated macrophages can be administered in situ at the wound or at the infarct site or at or near a site of injury of the CNS, but any other suitable mode of administration, particularly intravenous, is also envisaged by the invention.

The present invention thus further provides a method of promoting axonal regeneration in the central nervous system (CNS) comprising administering to a patient in need an effective amount of human mononuclear phagocytic leukocytes of the present invention at or near a site of injury of the CNS that results in or is accompanied by axonal damage.

In a preferred embodiment, the activated mononuclear phagocytic leukocytes are autologous, the injury is spinal cord injury, and the treatment is performed during surgery and includes administration of the cells to the patient into the spinal cord parenchyma, at the lesion site.

The present invention also provides a method of wound healing, particularly of chronic skin ulcers such as in diabetic wound ulcer and chronic leg ulcer, comprising administering to a patient in need an effective amount of mononuclear phagocytic leukocytes of the present invention into the wound.

The present invention still further provides a method of reduction of the volume of the necrotic tissue in cases of myocardial infarction comprising administering to a patient in need an effective amount of mononuclear phagocytic leukocytes of the present invention into the myocardium in situ, preferably relatively early in the process of the infarction.

The invention will now be illustrated by the following examples, which are non-limitative.

EXAMPLES

Example 1

Tissue Specimen Collection from the Patient

Blood and skin specimens are collected from the patient approximately one day before administration of the final cellular therapy product. About 200-250 ml of blood are collected into a blood-collecting bag containing anticoagulant. A segment of about 15 cm$^2$ (as measured at the upper surface of the skin) of full-thickness skin (epidermis and dermis) is harvested from the same patient and transferred into a container of a "washing solution" consisting of IMDM and antibiotics (16 µg/ml ofloxacin, 20 µg/ml vancomycin and 50 µg/ml gentamicin). The blood and skin specimens are transferred in separate, thermally isolated cases (interior temperature of the cases: 1-10° C. for blood and up to 38° C. for the skin) to a Cell Processing Center and are processed in a dedicated clean room facility (all procedures are performed in a class 100/ISO class 5 (Federal Standard 209E/ISO 14644-1) biological safety cabinet, which is located in a class 10,000/ISO class 7 clean room).

Example 2

Monocyte Isolation

Whole blood is diluted with phosphate-buffered saline (PBS). The diluted blood is layered onto Ficoll-Paque® PLUS (Amersham-Pharmacia Biotech, Sweden) (density: 1.076-1.078 g/ml at 20° C.) in centrifuge tubes and centrifuged to obtain the mononuclear cell fraction. The mononuclear cells are then washed three times with PBS. An aliquot from the second PBS wash, containing supernatant and $10^5$ cells, is removed and tested for sterility. The washed fraction of cells is layered onto Percoll® gradients, which are prepared by prior centrifugation. The monocyte-enriched fraction is obtained by centrifugation of the cells through the Percoll gradient. This fraction is washed with PBS and then resuspended in IMDM until proceeding to the incubation step. An aliquot from the PBS wash, containing supernatant and $10^5$ cells, is withdrawn for sterility testing. In addition to the sterility tests, the monocyte isolation process is monitored by conducting quality control tests, which include viable cell count (Trypan Blue dye exclusion), and the following baseline tests: culture purity (% CD14$^+$ cells), mannose receptor (MR) expression, IL-1β, ICAM-1 expression on cell membrane (all three tests are performed by flow cytometry), and morphological observation/cytoplasmic granules count.

Example 3

Processing of the Skin Tissue

On arrival at the Cell Processing Center, the skin container containing the full-thickness skin tissue specimen, is placed into the freezer (−18° C.) for at least one hour. After this period, the skin container is placed in the incubator (36-38° C.) for thawing, to enable easier elimination of the erythrocytes. After thawing, the skin container is transferred to the class 100 biological safety cabinet. The skin specimen is removed from the initial container and then soaked in a vessel of fresh washing solution (containing IMDM and antibiotics, see Example 1 above) for a short period. The soak is repeated with a new vessel of washing solution. The skin is then cut into segments, and the epidermis is removed and sampled for microorganism identification (see below). One dermis segment is cut into two ~2 mm² pieces to be taken for sterility tests. The dermis segments are soaked in a vessel containing fresh washing solution and sonicated for about 30-60 minutes by placing the vessel in an ultrasonic bath with the frequency of 35-40 kHz. The dermis tissue is then transferred into a new sterile container with fresh washing solution and soaked for at least 4.5 hours at 36-38° C. The main purpose of this procedure is to minimize the risk of bacterial contamination during the incubation with the monocytes. Before co-incubation with the monocytes, the dermis segments are washed twice with fresh medium (without antibiotics). The two ~2 mm² pieces are taken for sterility test.

Example 4

Incubation of the Isolated Monocytes with Dermis Tissue

The monocyte-enriched cell fraction of Example 2 above is placed in IMDM in sterile 50 ml tubes or tissue culture flasks (9 to $100 \times 10^6$ cells per container). Two dermis segments are added to each tube. A "parallel culture" tube is prepared containing 4.5 to $5.5 \times 10^6$ cells and one dermis segment. All tubes are incubated at 36-38° C. in a static 5% $CO_2$ humidified incubator for up to 38, preferably up to 24, hours (the "parallel culture" tube is incubated for 16.5-17.5 hours). The first evaluation of the development of the culture is performed after approximately 17 hours incubation. The "parallel culture" labeled tube containing incubated macrophages and dermis is removed from incubation and the culture is stopped. The dermis is discarded and the cell culture assessed for culture purity (% $CD14^+$ cells on flow cytometry) and viability (using the Trypan Blue dye exclusion method). The incubation period of the tubes containing the main culture is ended after 20.5 to 21.5 hours of incubation.

At the end of the incubation period, the dermis segments are removed from the main culture tubes using sterile forceps, and discarded. The incubated cells are sedimented by centrifugation, and a sample of incubation supernatant is tested for endotoxins and Gram stained for detection of bacteria. The cell pellets are pooled, washed, and re-suspended in IMDM. Cell counts and quality control tests such as viability, microscopic morphology, culture purity (% $CD14^+$ cells), mannose receptor expression, ICAM-1 expression, cytokine secretion and morphometric analysis/count of granules are performed. An aliquot containing $10^5$ incubated cells is added to a sample of the incubation supernatant for sterility testing. One sample containing supernatant and $5 \times 10^5$ cells is sent for *Mycoplasma* detection. After receiving the cell culture purity results, the cells are counted and then washed again using IMDM without phenol red. The cell pellet is then re-suspended, using IMDM without phenol red, to the final volume of the cell preparation. Qualification of the final cellular product to be administered to the patient is based on the concordance of the quality control test results to the pre-defined specifications.

Example 5

Preparation of the Final Cellular Therapy Product

The final cell therapy product consists of cells suspended in IMDM without phenol red, in a concentration of about 15,000-75,000, preferably 30,000-40,000, macrophages per μl. The final dose consists of 1-10, preferably 5-7 million macrophages, and is loaded into a syringe.

Example 6

Quality Control Procedures and Assays

6a. Raw Materials and Packaging Components

Raw materials and packaging components used in the production of the cells are subjected to appropriate quality control evaluations, in accordance with written standard operation procedures (SOPs), before they are accepted for use in the manufacturing process.

6b. Process Control—Biological Activity and Safety Tests

This example reviews the principal biological and safety features of the incubated human macrophage culture. The final cellular product specifications presented here are based on results obtained in assays for the determination of these characteristics, using heterologous and autologous blood and skin tissues from healthy subjects as well as autologous tissues from the patients treated until now. Macrophages are notorious for their versatility, but their activity does not probably depend upon interaction with specific antigens, and they perform their tasks during wound-healing irrespective of the cause of the damage.

An "In Process Control Plan" was established to control the production process and ensure the integrity of the final cellular therapy product. The cell culture is sampled at various stages during the manufacturing process and tested for bacterial and fungal contamination. These tests assess the sterility and endotoxin levels of the cellular therapy product. In addition, the cells are monitored for morphological characteristics and for viability. The cell culture undergoes sampling to assess immunological characterization, culture purity and biological activity. The yield of the production process is also monitored and recorded.

The final cellular therapy product must pass the lot release specifications. Each patient's cell product is an independent lot. The criteria include specifications for cell surface CD14 marker (tested by flow cytometry), cellular morphology (under the microscope) and cell granularity analyzed morphometrically, ELISA assay for quantification of IL-1β, culture viability (Trypan Blue dye exclusion), endotoxins and Gram stain. Interim sterility results of in-process samples are also part of the release quality control tests. Failure to meet the release specifications results in lot rejection. Additional assays are performed, e.g., mannose receptor and ICAM-1 expression tested by flow cytometry, Interleukin-6 (IL-6) secreted by the macrophages assayed by ELISA and *Mycoplasma* detection. The release criteria do not include specifications for these parameters.

To assess product sterility, aliquots from different stages of the production process are taken for sterility testing. Daily examination of the contents of the sterility-media vessels is performed during the sterility test incubation period, and any positive result, which indicates that the sample is not sterile, are immediately reported to the physician.

Microorganism detection and identification tests are carried out on the epidermis separated during skin preparation. These cultures are expected to contain contamination (probably normal skin flora), and thus this is not a basis for disqualification of the product. Microorganisms detected in these cultures are isolated, identified and tested for sensitivity to antibiotics.

Tissues, supernatants and cells are removed and tested for sterility at the following stages: dermis segments (prepared and ready for co-incubation); mononuclear cell isolation (after Ficoll separation): supernatant and cells; monocyte-enriched fraction isolation (after Percoll separation): supernatant and cells; and incubated macrophage preparation (after co-incubation): supernatant and cells. In addition to these sterility tests, the patient blood (before the isolation procedure) is sampled for *Mycoplasma* detection.

Example 7

Description of Quality Control Tests

Routine Safety Tests
7a. Sterility
Samples are tested for sterility in accordance with 21 CFR 610.12 [FDA "General Biological Products Standards"] using either the Direct Transfer Method or the Filter Method, according to the type of the sample.

In the Direct Transfer Method, each sample is divided into two portions. Each portion is introduced into a container with a suitable medium (Soybean-Casein Digest Medium or Thioglycollate Fluid Medium), the containers are closed and incubated at the appropriate temperature (20-25° C. for the Soybean-Casein Digest, and 30-35° C. for the Fluid Thioglycollate) and time (14 days).

In the Filter Method, the samples are filtered through a filter unit mounted on a canister. The sample is divided into two portions and each portion is filtered trough a distinct filter unit. Each filter is rinsed with rinsing fluid, and suitable media (Soybean-Casein Digest and Fluid Thioglycollate) is added—one type of media to each canister. Each canister is sealed and incubated at the appropriate temperature and time (as described above).

The sample of the invention tested for sterility (referred to also as the "inoculum") is inoculated into a vessel containing the test medium (thioglycollate or the soybean-casein digest), mixed thoroughly and incubated at the appropriate temperature (thioglycollate is incubated at 30-35° C., soybean-casein digest is incubated at 20-25° C.) for 14 days. Vessels containing samples (and sterility test media) of the second PBS wash of the mononuclear cells ($+10^5$ cells), the PBS wash of the monocyte enriched fraction ($+10^5$ cells) and the processed dermis before the co-incubation are examined visually for evidence of growth one day after inoculation. Turbidity or cloudiness in the test media at this stage is considered evidence of microbial contamination and results in disqualification of the product.

All the samples are further assessed for sterility by inspecting daily over the whole 14-day incubation period. The cultures are considered sterile if there are no signs of visible turbidity at the time of inspection.

A batch can be administered to a patient only if no microorganism contamination is identified. Following incubation, the cultures are examined for evidence of microbial growth. If colonies are found, they are Gram stained, and then tested with various biochemical tests used to identify specific organism types.
7b. Bacterial Endotoxins
The bacterial endotoxin test is performed using the lyophilized *Limulus Amebocyte* Lysate (LAL) (Associates of Cape Cod, Catalogue No. G5003 or G2003 (PYROTELL)), and/or the lyophilized *E. coli* Control Standard Endotoxin (Associates of Cape Cod, Catalogue No. E005)(actual value is stated by the producer for each batch). The product release specification is <200Eu/ml.

7c. Gram Staining
A batch can be administered to a patient only if the Gram stain result is negative.
Biological Activity Tests
7d. Viable Cell Count
Cell viability is determined using the Trypan Blue dye staining exclusion method. This method is based on the principle that live cells do not take up the dye, whereas dead cells do. Staining also facilitates the visualization of cell morphology. The Trypan Blue solution 0.4% (w/v) is mixed with a sample of cell suspension and transferred to a hemocytometer. The cells are counted under a microscope using the ×400 magnification. The batch is released for use if culture viability is $\geq 80\%$.
7e. Cell Morphology and Cytoplasmic Granules Count
Cell morphology is a qualitative assay assessed by microscopy using the ×400 magnification. The parameters examined are size, granularity and irregularity of the cells in culture. Samples of the monocyte-enriched fraction are taken for microscopic examination after Percoll separation and cell wash (time 0), and after the termination of the co-incubation. Comparison between cells before and after the incubation period is performed. After the incubation, the cells should appear relatively large, irregular and granulated.

Cell granularity has been observed to be a very specific feature of the culture after incubation. Under the phase microscope, these granules appear as highly refractive spherical objects with a bluish hue that can be easily counted. The granules are rare in the cells before the incubation, but are prevalent after incubation, and are probably specifically induced by incubation and manipulation of the culture. The aim of the analysis of the granules is to obtain a numerical measure of the incidence of cytoplasmic granules in the incubated macrophages. The analysis provides a robust result that can be available well within the time needed to perform the other quality control tests and product packaging operations.

Counting of the granules is performed by analysis of computer images. Initially, the granularity value was expressed by the average number of granules per cell in the sample. However, after analyzing a large number of batches, it was found that the granules are not distributed normally between cells, and that the granularity of the culture is best represented by the number of granules per cell in the 25% most granular cells (the top quartile). The top quartile was chosen after considering the median and other quartiles. Of these, the threshold granularity of the top quartile was found to have the lowest batch-to-batch coefficient of variation and to be the most sensitive in showing statistically meaningful differences between cells before vs. after incubation. The results are shown in Table 1.

TABLE 1

Count of cell granules before and after incubation

| | Number of granules/cell before incubation | | Number of granules/cell after incubation | |
|---|---|---|---|---|
| | Average | Top quartile threshold | Average | Top quartile threshold |
| Batches counted | 19 | 18 | 21 | 20 |
| Min-Max | 0.5-4.2 | 1.0-5.3 | 2.0-12.4 | 3.0-15.8 |
| Average | 2.5 | 3.5 | 7.6 | 10.4 |
| Standard deviation | 1.1 | 1.2 | 2.4 | 3.4 |

Based on the results, cell granularity of $\geq 4$ granules per cell in the top quartile (i.e. at least 4 granules in 25% of the most granular cells) is used as a parameter required for the final product to be used in patients. All the clinical batches analyzed by this method and the majority of the research batches contained at least 4 granules per cell in the top quartile. The choice of the granularity threshold of the top quartile as the measured parameter and 4 granules per cell as the minimum threshold value is based on the need to maximize sensitivity to the difference between the cells before and after the incubation, using a sample size of at least 60 cells. The chosen parameter is the parameter with the lowest coefficient of variance when examined across many batches. This maximizes the sensitivity to true differences between samples (e.g. between cells after vs. before incubation).

For counting the granules, samples are withdrawn from freshly-prepared 'monocyte-enriched' fraction (before incubation) and a day later from the 'incubated cells' fraction (after incubation). Microscopy of each fraction is carried out on the fresh samples. Samples are placed on a microscope slide and then left for at least 15 minutes to allow the cells to settle, thus improving the focus that can be obtained under the microscope. The cells are inspected using a microscope with ×100 objective and phase contrast, and imaged with a digital camera. The sample area under the cover slip is divided into 4 quadrants; each quadrant is scanned through systematically to avoid viewing the same cells twice. Cells are photographed as they come into the field of view until 15 cells have been photographed in each quadrant. This gives pictures of 60 cells for each sample. In each field photographed, the focus is adjusted to maximize the number of granules that can be seen. The digital images are transferred to a computer for storage and subsequent analysis. Pictures of cells are analyzed by image analysis software and granularity is assessed. Counting of the granules is performed by analysis of computer images by image analysis.

There is a highly significant increase in granules following incubation of the cells with dermis in all batches. Results show that granularity increases on average more than 200% in cells incubated with dermis.

It can be concluded that cell granularity is one of the parameters that reflects the change in phenotype that the macrophages undergo during incubation.

FIGS. 1A-1B are photographs of a non-granulated monocyte (before incubation) and of a granulated monocytic leukocyte (after incubation), respectively.

7f Culture Purity —CD14 Assay by Flow Cytometry

The purity of cell cultures is monitored by flow cytometry using monoclonal antibodies (mAbs) directed to human CD14, a well-established cell surface marker specific for human monocytes/macrophages. The cells are labeled by challenging with the commercially available fluorochrome-conjugated mAb, and then washed with PBS. The fraction of cells positive for CD 14 is regarded as a measure of culture purity. The parameter is assayed both before and after the incubation stage. The purity of the Incubated Macrophages cell culture serves as a product release criterion and should be >40%, preferably 60% or more CD 14$^+$ cells.

7g. Mannose Receptor Expression Assay

The mannose receptor (MR) is a carbohydrate-binding membrane protein, which is involved in the phagocytosis of yeast cells. Presence of the mannose receptor on the cell surface is determined by flow cytometry using a commercially available fluorochrome-conjugated mAb specific for the human mannose receptor. The cells are incubated with the mAb, and washed as described above. The fraction of cells positive for mannose receptor is considered to indicate the potential phagocytic activity of cells as well as cell maturation. This assay is performed both before and after incubation of the cells.

In order to increase the ability to detect small, but significant, increments in the MR expression, cells obtained from the "Monocyte-Enriched Fraction" (before the co-incubation with dermis) are tested in triplicate. Cells obtained after the coincubation with dermis are tested in duplicates. In this way, two independent sets of three and two measurements, respectively, are statistically analyzed.

The array of two MR expression measurements at 21 hours (after the co-incubation stage) is compared to the array of three measurements performed at time 0 hours. A t-test analysis is performed and the significance of the difference (increase at 21 hours as compared to 0 hours) determined at the 95-confidence level. A statistically significant increase in the MR expression occurring in the post-incubated cells as compared to the pre-incubation levels is meaningful, and indicates that the cell culture underwent the specific triggering needed and will continue to develop neuroregenerative phenotypes in vivo.

7h. ICAM-1 Expression Assay

The interaction between cells is mediated in part by families of adhesion molecules. Intercellular adhesion molecules (ICAMs) are structurally related members of the immunoglobulin supergene family and are ligands for the β2 integrin molecules present on leukocytes. ICAM-1 is expressed constitutively on endothelial cells and on some lymphocytes and monocytes. Its expression is significantly increased in the presence of cytokines (TNFα, IL-1β, and IFN-γ), thus showing a correlation with cell activation. Furthermore, ICAM-1 has been reported to act as a co-stimulatory signal in myelin uptake by macrophages after nerve injury (Vougioukas et al., 2000, Involvement of intercellular adhesion molecule-1 in myelin recognition by macrophages. Acta Neuropathol (Berl), 99: 673-79).

The expression of the ICAM-1 receptor on the CD14$^+$ cells is measured by immunolabeling the cells with commercially available specific mAb and analysis with flow cytometry. The expression of the ICAM-1 receptor is enhanced in cells after co-incubation with skin.

7i Interleukin-1β Assay

Production of IL-1β is a direct result of the monocytes incubation with dermis and this cytokine is secreted by the macrophages in the final product. The IL-1β levels are assessed according to the following procedure: 1.4×10$^6$ co-incubated cells are transferred to a sterile test tube, centrifuged and re-suspended in IMDM. The cell suspension is incubated for 30 minutes at 36-37° C. in a humidified 5% CO$_2$ incubator. At the end of the 30-minute incubation stage, the tube is centrifuged and the level of IL-1β is determined in the supernatant by ELISA, using commercially available kits. The results are calculated per million macrophages, determined as CD 14+cells. Results of at least 17 pg/10$^6$ CD14$^+$ cells are acceptable.

7j. BDNF Assay

The level of BDNF was determined in cell-conditioned medium by ELISA, using commercially available kits, e.g. Human BDNF DuoSet Elisa development System (R&D catalog No. DY248).

Human blood-borne monocytes were isolated and incubated with dermis as described above. After incubation, cells were harvested by centrifugation (380×g, 10 min, 10° C.). Cell conditioned medium was prepared by re-suspending 1.4 million harvested cells in 1.4 mL fresh IMDM and incubation for 30 minutes at 37° C. in a humidified incubator (5% $CO_2$). The medium was then acidified (by addition 56 μL of 1M HCl) and neutralized after 5 minutes with 56 μL of 1M NaOH. The decanted conditioned medium was collected after sedimentation of the cells by centrifugation and frozen at −70° C. until assayed.

Other neurotrophins such as NT-3 and NT-4 can be assayed in these samples using the suitable commercial ELISA assay kits from the same provider of the BNDF kit.

7k. IL-6 Assay

The level of IL-6 was determined in the supernatant of the monocytes before incubation and of the obtained activated macrophages by ELISA, using commercially available kits. Secretion of the cytokine IL-6 by macrophages after incubation is enhanced 4-15 fold over the level in pre-incubated monocytes.

Example 8

Activated Macrophages Promote Partial Sensory and Motor Functional Recovery in Humans with Complete Spinal Cord Injury In phase I clinical trial, eight patients with complete spinal cord injury (classified as ASIA A according to the American Spinal Cord Injury Association), were treated with direct injection of 4,000,000 autologous macrophages (after incubation with dermis as described in the examples above) into the spinal cord at the lesion site. Three of them recovered motor and sensory function and were reclassified as ASIA C. Demographic and data related to the type of the injury are presented in Table 2. Motor and sensory scores, ASIA classifications of patients enrolled in the study on admission (initial) and on the latest follow-up visit, are shown in Table 3 below. Light touch, pinprick (pain) and motor recovery are expressed as the % increase as compared to the initial examination.

According to the clinical findings obtained to date, no adverse events that could be associated with the therapy have occurred.

Initial signs of clinical efficacy have been observed. Significant sensory recovery and some motor recovery has been found in three patients, with Patient #1 achieving bladder control as well.

TABLE 2

Characteristics of the patients with complete spinal cord injuries who were treated by local injection of autologous activated macrophages.

| Patient number | Cause of injury | Sex | Age | Neurological level | Day of treatment after injury | Month of latest follow-up examination |
|---|---|---|---|---|---|---|
| 1 | Vehicle accident | F | 19 | T6 | 14 | 21 |
| 2 | Fall | M | 31 | C6 | 11 | 15 |
| 3 | Vehicle accident | M | 30 | T6 | 9 | 15 |
| 4 | Sport accident | M | 20 | T6 | 12 | 10 |
| 5 | Fall | M | 41 | T11 | 14 | 6 |
| 6 | Vehicle accident | M | 24 | T6 | 14 | 6 |
| 7 | Vehicle (sport accident) | M | 19 | T5 | 14 | 4 |
| 8 | Vehicle accident | M | 26 | T5 | 10 | 6 |

TABLE 3

Motor and sensory scores and ASIA classifications of patients enrolled in the study on admission (initial) and at the latest follow-up visit.

| Patient Number | Follow-up (months) | ASIA Grade | | Motor Score | | | Light-touch Score | | | Pinprick Score | | |
|---|---|---|---|---|---|---|---|---|---|---|---|---|
| | | Initial | Latest | Initial | Latest | % recovery* | Initial | Latest | % recovery* | Initial | Latest | % recovery* |
| 1 | 21 | A | C | 50 | 72 | 44 | 57 | 81 | 42 | 53 | 81 | 53 |
| 2 | 18 | A | C | 20 | 34 | 70 | 40 | 77 | 92 | 40 | 68 | 70 |
| 3 | 15 | A | C | 50 | 55 | 10 | 54 | 74 | 37 | 53 | 76 | 43 |
| 4** | 10 | A | A | 45 | 50*** | — | 52 | 52 | 0 | 48 | 52 | 8 |
| 5** | 6 | A | A | 50 | 50 | 0 | 66 | 72 | 9 | 66 | 67 | 1 |
| 6 | 6 | A | A | 46 | 46*** | 0 | 49 | 54 | 10 | 44 | 50 | 14 |
| 7 | 4 | A | A | 50 | 50 | 0 | 47 | 51 | 9 | 46 | 48 | 4 |
| 8 | 3 | A | A | 40 | 50*** | — | 50 | 50 | 0 | 48 | 55 | 15 |

*Relative to the initial examination.
**Intra-operative visualization revealed severe liquefaction of the cord.
***The motor scores in these three patients are affected by upper limb injuries in addition to the spinal cord injury.

These results indicate that autologous co-incubated human macrophages exhibit wound-healing phenotypes as demonstrated by in vitro assays. Furthermore, these macrophages are shown to promote regeneration of the CNS of humans as an example of the ability of these cells to promote wound healing in other tissues.

Example 9

Efficacy of Administration of Cultured Macrophages as a Therapy for Acute myocardial infarction The following protocol is used to test the effect of activated macrophages in two groups of Sprague-Dawley (SD) male rats weighing 300±20 grams (Harlan Laboratories, Israel]: Group A (12 rats) rats are treated with a 25 µl suspension containing $2.5 \times 10^6$ macrophages and DCCM1 medium, and Group B (six rats) rats are treated with 25 µl of DCCM1 medium only.

The activated rat macrophages are produced in accordance with the procedures as described herein or as described in U.S. Pat. Nos. 5,800,812, 6,117,424 and 6,267,955, Prior to administration, macrophages cultures are tested for purity and activity by flow cytometry.

Myocardial ischemia is induced in the SD rats by ligation of a coronary artery. The resulting necrotic tissue has an approximate volume of 50 mm$^3$, which is approximately 6-fold the size of the spinal cord stump that we usually treat in other experiments with about 400,000 activated macrophages suspended in 5 µl DCCM1 medium.

The activated macrophages are implanted in the SD rats in a blind fashion, by the surgeon. An approximately sixfold dose of activated macrophages is used in comparison with the amount of about 400,000 cells used to treat rats after spinal cord transection. Therefore, an extrapolated total effective dose of 2.5 million activated macrophages suspended in 25 µl DCCM1 medium is divided into 5 doses and injected into the myocardium immediately after induction of the infarct: one injection in the center of the infarct is performed followed by four additional injections at the border between the infarct and the healthy tissue. The injections are performed with a Hamilton syringe, through a 22 G needle. Animals are left to recover in the animal's room, allowing free access for eating and drinking, and in a 12/12 h light/dark cycle. Follow-up of the results is continued for 6 weeks. Survival rate is a key parameter in this study.

Assessment of the results is done in a blind fashion, Histological evaluation is performed on cross sections from the left ventricle (LV) to assess infarct area, LV cavity diameter, and LV mass area using Masson trichrome stained slides. TUNEL stained slides are used to assess apoptotic cell death. Specific staining for macrophages is performed to assess existence and localization of macrophages within normal, border, or infarcted myocardium. Mitotic index is measured by immunohistochemical staining with specific monoclonal antibodies for proliferating cell nuclear antigen (PCNA). For data analysis, statistical analysis is performed on each parameter.

The invention claimed is:
1. A process for making activated human mononuclear phagocytic leukocytes suitable for human administration, the method comprising:
(i) suspending monocytes isolated from a blood sample of a human individual in a medium suitable for cell culture;
(ii) processing human skin segments obtained from the same individual by:
(A) freezing said skin fragments, thawing and soaking them in a medium suitable for cell culture and containing antibiotics,
(B) removing the epidermis from the skin fragments and cutting them into segments, yielding human dermis segments,
C) sonicating the human dermis segments in a medium suitable for cell culture and containing antibiotics, yielding sonicated dermis segments,
(D) soaking the sonicated dermis segments in fresh medium suitable for cell culture and containing antibiotics, and
(E) rinsing the dermis segments with fresh medium suitable for cell culture;
(iii) activating the isolated monocytes suspended in step (i) by coincubating them with the rinsed human dermis segments resulting from step (ii), thus obtaining an incubation mixture containing activated human mononuclear phagocytic leukocytes;
(iv) removing the human dermis segments from the incubation mixture resulting from step (iii) and sedimenting the obtained activated human mononuclear phagocytic leukocytes by centrifugation; and
(v) washing and resuspending in fresh medium suitable for cell culture, the activated human mononuclear phagocytic leukocytes resulting from step (iv), thus obtaining a culture of activated human mononuclear phagocytic leukocytes;
wherein at least 80% of the activated human mononuclear phagocytic leukocytes are viable according to a Trypan Blue exclusion assay;
wherein the suspension of activated human mononuclear phagocytic leukocytes comprises less than 200 Eu bacterial endotoxin per mL of suspension;
wherein the activated human mononuclear phagocytic leukocytes in the top quartile of granularity contain at least 4 granules per cell;
wherein at least 40% activated human mononuclear phagocytic leukocytes express CD14; and
wherein the activated human mononuclear phagocytic leukocytes produce at least 17 pg interleukin-1β per $10^6$ activated human mononuclear phagocytic leukocytes expressing CD14.

2. The process according to claim 1, wherein the upper surface of the human dermis segments obtained in step (ii)(B) each have an area of about 0.1 to 5 cm$^2$.

3. The process according to claim 2, wherein the step (ii)(C) comprises transferring the dermis segments to a sterile container and immersing said dermis segments in said medium suitable for cell culture and containing antibiotics, introducing the container into an ultrasonic bath containing de-ionized water and sonicating.

4. The process according to claim 2, wherein the upper surface of the human dermis segments obtained in step (ii)(B) each have an area of about 0.5 to 2 cm$^2$.

5. The process according to claim 1, wherein each said medium suitable for cell culture is IMDM or RPMI 1640 and said antibiotics, when present, are a combination of ofloxocin, vancomycin and gentamicin.

6. The process according to claim 1, wherein said step of sonicating the dermis segments of step (ii)(C) is performed at the frequency of 35-40 kHz.

7. The process according to claim 1, wherein, in step (iii), the incubation of the monocytes with the human dermis segments is carried out at about 36-38° C. in an atmosphere of 5% $CO_2$, for up to 38 hours.

8. The process according to claim 7, wherein, in step (iii), the incubation of the monocytes with the human dermis segments is carried out at about 36-38° C. in an atmosphere of 5% $CO_2$, for up to 24 hours.

9. The process according to claim 1, wherein the activated human mononuclear phagocytic leukocytes also exhibit one or more of the properties selected from the group consisting of:
   (a) a statistically significant increase in mannose receptor expression compared to the monocytes originally isolated from the blood sample of step (i);
   (b) expression of ICAM-1 receptor with geometric mean fluorescence of about 200 or higher as measured by flow cytometry;
   (c) secretion of more than 10 pg BDNF per $10^6$ $CD14^+$ activated human mononuclear phagocytic leukocytes; and
   (d) an about 4-15 fold increase in IL-6 secretion compared to the monocytes originally isolated from the blood sample in step (i).

10. A method of promoting axonal regrowth in the injured spinal cord of a human individual, comprising:
   manufacturing a culture of activated human mononuclear phagocytic leukocytes suitable for human administration by:
      (i) suspending monocytes isolated from a blood sample of a human individual in a medium suitable for cell culture;
      (ii) processing human skin segments obtained from the same individual by:
         (A) freezing said skin fragments, thawing and soaking them in a medium suitable for cell culture and containing antibiotics,
         (B) removing the epidermis from the skin fragments and cutting them into segments, yielding human dermis segments,
         (C) sonicating the human dermis segments in a medium suitable for cell culture and containing antibiotics,
         (D) soaking the sonicated dermis segments in fresh medium suitable for cell culture and containing antibiotics, and
         (E) rinsing the dermis segments with fresh medium suitable for cell culture;
      (iii) activating the isolated monocytes suspended in step (i) by coincubating them with the rinsed human dermis segments resulting from step (ii), thus obtaining an incubation mixture containing activated human mononuclear phagocytic leukocytes;
      (iv) removing the human dermis segments from the incubation mixture resulting from step (iii) and sedimenting the obtained activated human mononuclear phagocytic leukocytes by centrifugation; and
      (v) washing and resuspending in fresh medium suitable for cell culture, the activated human mononuclear phagocytic leukocytes resulting from step (iv), thus obtaining a culture of activated human mononuclear phagocytic leukocytes;
   wherein at least 80% of the activated human mononuclear phagocytic leukocytes are viable according to a Trypan Blue exclusion assay;
   wherein the suspension of activated human mononuclear phagocytic leukocytes comprises less than 200 Eu bacterial endotoxin per mL of suspension;
   wherein the activated human mononuclear phagocytic leukocytes in the top quartile of granularity contain at least 4 granules per cell;
   wherein at least 40% activated human mononuclear phagocytic leukocytes express CD14; and
   wherein the activated human mononuclear phagocytic leukocytes produce at least 17 pg interleukin-1β per 106 activated human mononuclear phagocytic leukocytes expressing CD14; and
   administering the culture of activated human mononuclear phagocytic leukocytes manufactured in said manufacturing step to the human individual with an injured spinal cord, in an amount effective to promote axonal regrowth in the injured spinal cord of said human individual, wherein the activated human mononuclear phagocytic leukocytes are administered into the spinal cord parenchyma of said human individual at or near the site of injury.

11. The method according to claim 10, wherein the activated human mononuclear phagocytic leukocytes are autologous to said human individual.

12. A process for making activated human mononuclear phagocytic leukocytes suitable for human administration, comprising:
   (i) suspending monocytes isolated from a blood sample of a human individual in a medium suitable for cell culture;
   (ii) processing segments of tissue-engineered skin or tissue-engineered skin equivalent by:
      (A) removing the epidermis, thus yielding dermis segments,
      (B) sonicating the dermis segments in a medium suitable for cell culture and containing antibiotics,
      (C) soaking the sonicated dermis segments in fresh medium suitable for cell culture and containing antibiotics, and
      (D) rinsing the dermis segments with fresh medium suitable for cell culture;
   (iii) activating the isolated monocytes suspended in step (i) by coincubating them with the rinsed dermis segments resulting from step (ii), thus obtaining an incubation mixture containing activated human mononuclear phagocytic leukocytes;
   (iv) removing the dermis segments from the incubation mixture resulting from step (iii) and sedimenting the obtained activated human mononuclear phagocytic leukocytes by centrifugation; and
   (v) washing and resuspending in fresh medium suitable for cell culture, the activated human mononuclear phagocytic leukocytes resulting from step (iv), thus obtaining a culture of activated human mononuclear phagocytic leukocytes,
   wherein at least 80% of the activated human mononuclear phagocytic leukocytes are viable according to a Trypan Blue exclusion assay;
   wherein the suspension of activated human mononuclear phagocytic leukocytes comprises less than 200 Eu bacterial endotoxin per mL of suspension;
   wherein the activated human mononuclear phagocytic leukocytes in the top quartile of granularity contain at least 4 granules per cell;
   wherein at least 40% activated human mononuclear phagocytic leukocytes express CD14; and
   wherein the activated human mononuclear phagocytic leukocytes produce at least 17 pg interleukin-1β per $10^6$ activated human mononuclear phagocytic leukocytes expressing CD14.

* * * * *